US008494175B2

(12) United States Patent
Maeda et al.

(10) Patent No.: US 8,494,175 B2

(45) Date of Patent: Jul. 23, 2013

(54) NOISE REDUCTION DEVICE AND NOISE REDUCTION SYSTEM

(75) Inventors: Tsuyoshi Maeda, Hyogo (JP); Yoshifumi Asao, Osaka (JP)

(73) Assignee: Panasonic Corporation, Osaka (JP)

( * ) Notice: Subject to any disclaimer, the term of this patent is extended or adjusted under 35 U.S.C. 154(b) by 326 days.

(21) Appl. No.: 13/045,732

(22) Filed: Mar. 11, 2011

(65) Prior Publication Data

US 2011/0222699 A1 Sep. 15, 2011

(30) Foreign Application Priority Data

Mar. 15, 2010 (JP) ................................ 2010-057081

(51) Int. Cl.
*A61F 11/06* (2006.01)
*G10K 11/16* (2006.01)
*H03B 29/00* (2006.01)

(52) U.S. Cl.
USPC ....... 381/71.4; 381/71.1; 381/71.2; 381/71.8; 381/73.1; 381/94.1; 704/226; 704/227; 704/228

(58) Field of Classification Search
USPC .................. 381/71.1, 71.2, 71.4, 71.8, 71.11, 381/71.12, 73.1, 94.1, 94.7, 56–59; 379/392.01; 704/226, 227, 228
See application file for complete search history.

(56) References Cited

U.S. PATENT DOCUMENTS 6,343,127 B1 * 1/2002 Billoud ........................ 381/71.4

FOREIGN PATENT DOCUMENTS

JP 01-270489 A 10/1989
JP 03-259722 A 11/1991

* cited by examiner

*Primary Examiner* — Vivian Chin
*Assistant Examiner* — Paul Kim
(74) *Attorney, Agent, or Firm* — Pearne & Gordon LLP

(57) ABSTRACT

A noise reduction device is disclosed, in which noise reduction device, a controlling sound generator outputs a white noise generated by a white-noise generator, and this white noise is sensed by an error sensor for identifying an acoustic transmission function covering a path from the controlling sound generator to the error sensor. At this time, an identification controller prompts the white noise generator to generate a white noise for identifying the acoustic transmission function provided that an ambient noise level sensed by the error sensor is not greater than a given threshold.

20 Claims, 18 Drawing Sheets

NOISE REDUCTION DEVICE AND NOISE REDUCTION SYSTEM

FIELD OF THE INVENTION

The present invention relates to noise reduction at seats, more particularly, it relates to a noise reduction device and a noise reduction system to be used in an aircraft or a railroad coach.

BACKGROUND OF THE INVENTION

In an aircraft or a coach where passengers are always involved with noises, the passengers in the seats sometimes cannot clearly catch information provided through audio, such as an in-flight notice, due to the noises around the seats.

The aircraft or the coach defines an interior space with continuous walls, so that the interior space forms a kind of enclosed structure. If noise sources exist inside and outside the interior space, the passengers in the interior space are to be confined within a regular noise environment. An excess noise sometimes invites physical or mental stress to the passengers, thereby degrading the convenience in the interior space. In the case of an aircraft, in particular, although flight attendants try to provide the passengers with good service in the interior space, this degradation in convenience becomes a critical problem to a service quality.

In the case of the aircraft, the following noises are chiefly involved: noises produced by the devices such as a propeller or an engine which generates thrust force for the aircraft, and noises, such as zip sound generated by the nose and the wings of the aircraft, involved with airstream produced by the movement of the aircraft in the air. The foregoing noises audible in the interior space make the passengers unpleasant and also hinder the in-flight audio notice. The noises thus need to be reduced.

Passive attenuating measures have been taken, in general, for reducing the noises in the enclosed space. This method places sound insulating material, such as a diaphragm or sound absorption material, between the enclosed structure and the noise source. The diaphragm includes, e.g. a high density diaphragm, and the sound absorption material includes, e.g. a sound absorption sheet. However, the acoustic absorption material has a high density and thus becomes a weight-gaining coefficient. An increment in the weight consumes a greater amount of fuel or reduces a flight range. As a result, the increment in the weight incurs degrading the economical and functional performances of the aircraft. On top of that, the foregoing materials have a problem of strength such as being subject to damages and a problem of design such as having a poor quality image.

Active attenuating measures have been taken for overcoming the foregoing problems caused by the passive attenuating measures, for instance, a method of generating an acoustic wave having an opposite phase to that of the noise is used generally for noise reduction. This method allows reducing the noise at the noise source or around the noise source, thereby preventing the noise from propagating to a region where noise reduction is needed. To be more specific, a noise reduction device described below has been proposed:

The noise reduction device comprising:

- a microphone for sensing a sound generated by a noise source;
- a controller for amplifying an electric signal supplied from the microphone and then reversing a phase of the electric signal; and
- a speaker for converting the electric signal supplied from the controller into sound and then outputting the sound.

This device is disclosed in Patent Literature 1.

To find an acoustic transmission function from a speaker to a noise controlling point is needed for designing an active noise reduction device. The transmission function is measured, in general, this way: A white noise having a flat frequency characteristic in a frequency control band is generated from the speaker, and a microphone placed at the control point senses this white noise. At this time, an external noise level is measured, and the white noise of which level is higher than the external noise level by a given amount, e.g. 10 dB, should be generated. This method is disclosed in Patent Literature 2.

The method disclosed in Patent Literature 2 can be used only in a case where one noise reduction device is installed, and the acoustic transmission function between the speaker and the microphone placed at the control point can be measured by the foregoing method. Patent Literature 2, however, keeps silent about a case where multiple noise reduction devices are installed. In an airplane, each one of seats is equipped with a noise reduction device, so that multiple noise reduction devices, i.e. in a quantity equal to the number of seats, need the acoustic transmission functions. In such a case, it is desired to measure fast the acoustic transmission functions of the respective seats, i.e. the noise reduction devices, free from being affected by external noises.

Related Art Literature

Patent Literature 1: Unexamined Japanese Patent Application Publication No. H01-270489

Patent Literature 2: Unexamined Japanese Patent Application Publication No. H03-259722

SUMMARY OF THE INVENTION

A noise reduction device of the present invention comprises the following structural elements:

- a noise sensor for sensing a noise;
- a controlling sound output section for generating a controlling sound based on a controlling sound signal, where the controlling sound is to be superposed on the noise at the control center of a control space for reducing the noise;
- a noise controller for generating a controlling sound signal; and
- an error sound sensor for sensing an error sound between the noise and the controlling sound.

The noise controller includes an identification sound generator and an identification controller. The controlling sound output section outputs an identification sound, which is then sensed by one of the error sound sensor and the noise sensor. In the case of identifying the acoustic transmission function which covers a path from the controlling sound output section to one of the error sound sensor and the noise sensor, the identification controller identifies the acoustic transmission function by generating an identification sound from the identification sound generator provided that an ambient noise level sensed by one of the error sound sensor and the noise sensor is not greater than a given threshold.

The structure discussed above allows identifying the acoustic transmission function fast and free from influence of external noises. For instance, in a case where noise reduction devices are installed at the seats adjacent to each other, and while a first noise reduction device of the devices identifies its acoustic transmission function, a second device of the devices halts its identifying action in order not to be affected by an identification sound from the first one, and the second one starts its identifying action after the first one finishes the identifying action. As a result, both of the first and the second noise reduction devices carry out the identifying action free from being affected by the identification sound from the adjacent noise reduction device.

A noise reduction system of the present invention comprises the following structural elements:

multiple noise reduction devices; and a server for supervising whether or not the multiple noise reduction devices identify their acoustic transmission functions.

Multiple noise reduction devices included in the noise reduction system start identifying actions sequentially following a given order of priority at intervals sufficiently shorter than an identifying time. While a subject noise reduction device undergoes the identifying action, the ambient noise level of a noise reduction device which is expected to undergo the identifying action next to the subject noise reduction device is sensed by one of the error sound sensor and the noise sensor, and in a case where the ambient noise level falls not greater than the given threshold, the next device starts the identifying action. Then an implementation of the identification is registered in the server. In a case where the ambient noise level sensed by one of the error sound sensor and the noise sensor is greater than the given threshold, the start of identifying action should be halted for a given time before the identifying action starts following the order of priority.

The foregoing structure allows a number of noise reduction devices to undergo the identifying actions simultaneously free from being affected by the identification sounds from other noise reduction devices during the identifying action, which can be thus carried out fast and accurately.

DESCRIPTION OF PREFERRED EMBODIMENTS Exemplary embodiments of the present invention are demonstrated hereinafter with reference to FIG. 1-FIG. 18.

Exemplary Embodiment 1

Figure 1:
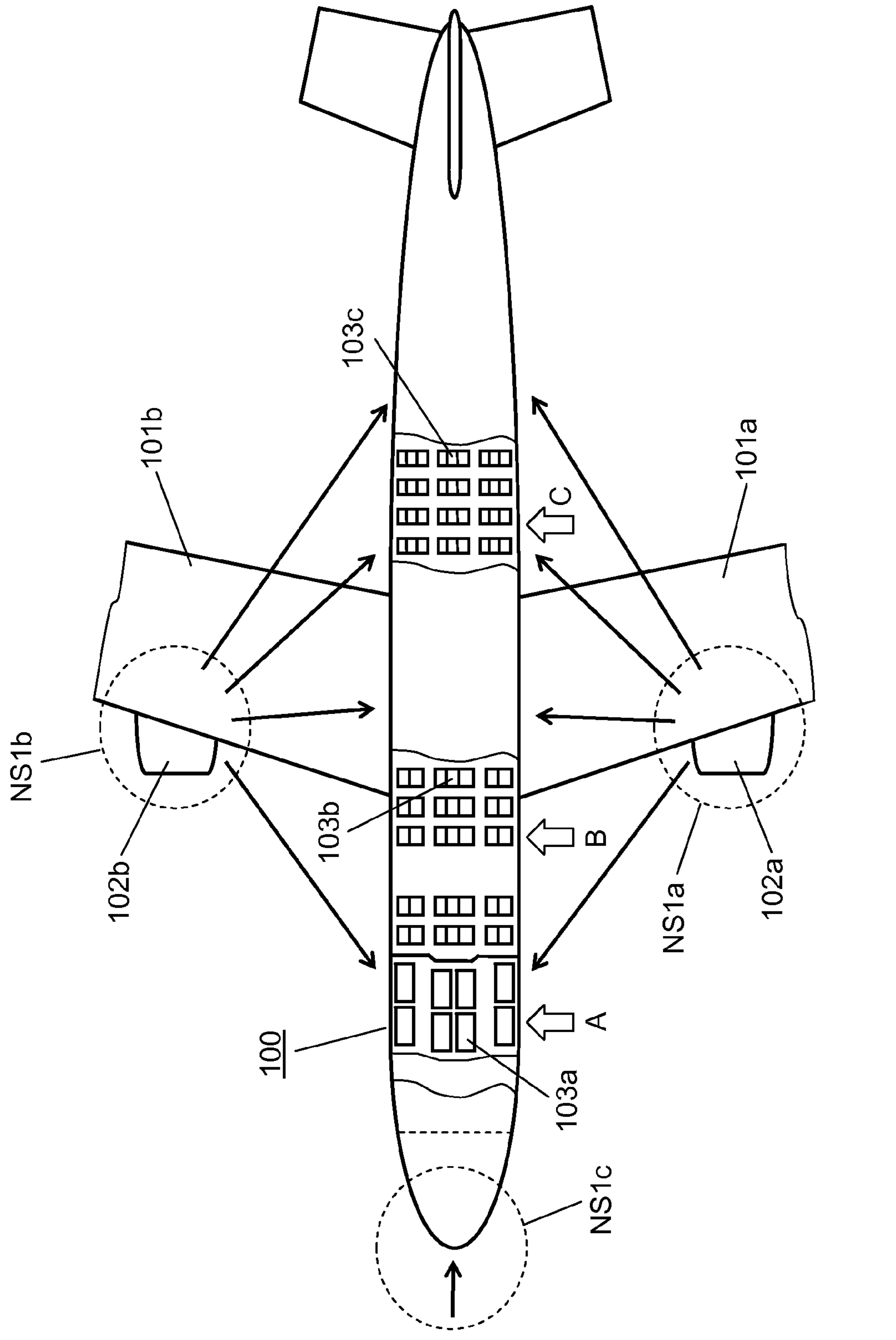
FIG. 1 is a plan view illustrating an installation environment of noise reduction devices in accordance with a first embodiment of the present invention.

A noise reduction device in accordance with the first embodiment of the present invention is demonstrated hereinafter when the device is installed in an aircraft. The sound environment in the aircraft that needs the installation of the noise reduction devices is described with reference to FIG. 1 and FIG. 2. FIG. 1 is a plan view illustrating an installation environment of the noise reduction devices in accordance with the first embodiment of the present invention. Aircraft 100 includes engines 102*a* and 102*b* on the left wing and the right wing respectively.

From the viewpoint of sound environment, the engine actually generates rotary sound, and the engine is a key coefficient of the noise source because it involves airstream reflection during the flight. From the viewpoint of service to passengers, engines 102*a* and 102*b* act as external noise sources NS1*a*, NS1*b* to every part of the aircraft such as seat rows 103*a*, 103*b*, and 103*c* installed in cabin A (e.g. first class), cabin B (business class), and cabin C (economy class) respectively. Another noise source NS1*c*, i.e. the aircraft moves in the air space at a high speed, so that zip sounds are produced by collision between the airstream and the nose of aircraft or the wings. This zip sound works as noise source NS1*c* and adversely affects in-flight services such as providing information.

Figure 2:
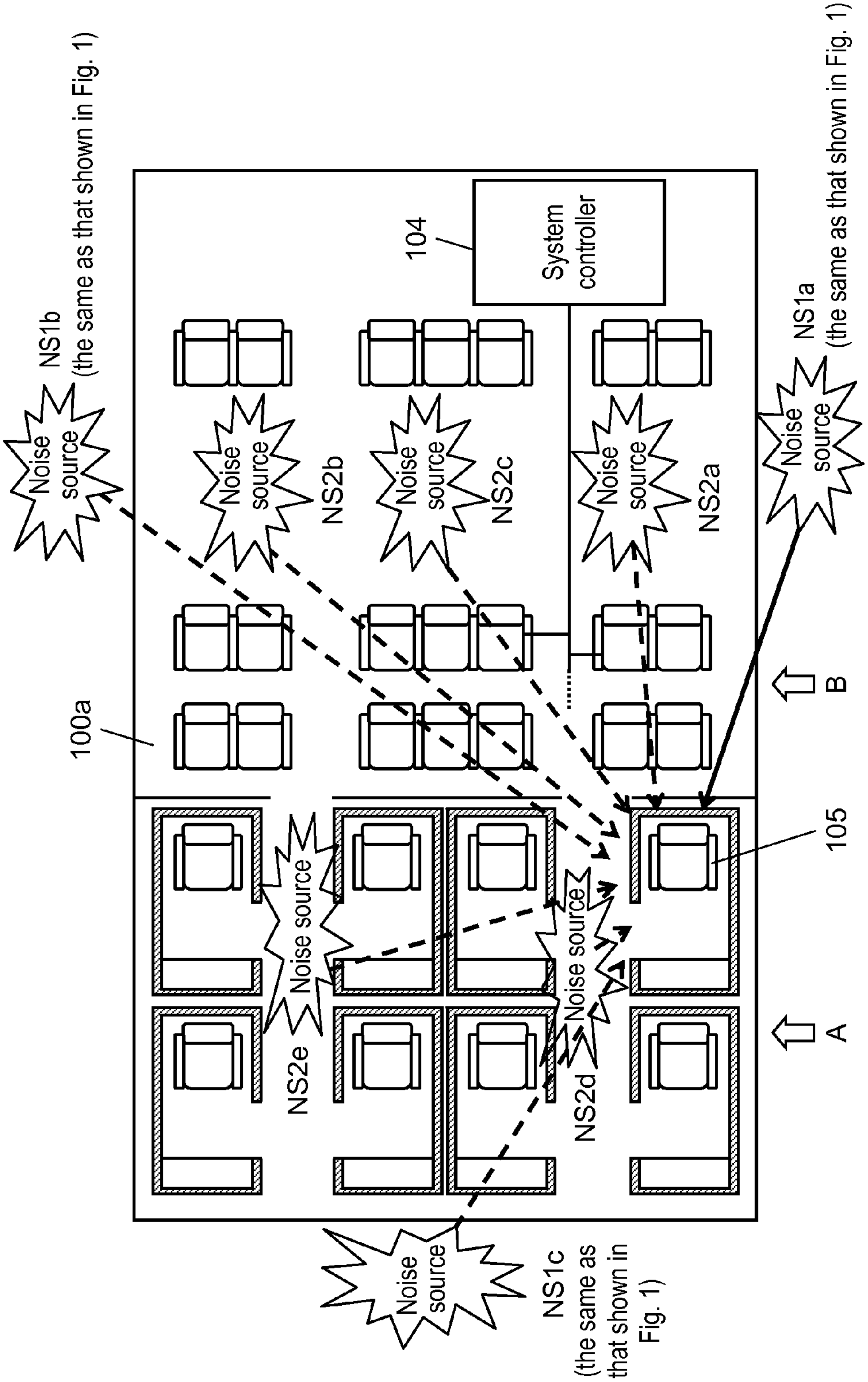
FIG. 2 is a plan view detailing an installation environment of the noise reduction devices in accordance with the first embodiment of the present invention.

FIG. 2 is a plan view detailing an installation environment of the noise reduction devices in accordance with the first embodiment of the present invention. In FIG. 2, parts of seat-arrangement in cabin A and cabin B shown in FIG. 1 are enlarged. Cabin 100*a* is split by a wall into cabin A and cabin B. Each one of the seat-rows is equipped with an audio-video device, and the audio-video devices are connected via a communication line such as Ethernet (registered trademark) to system controller 104 that includes a switching device, a control server.

Cabin 100*a* is situated in the sound environment where noise sources NS1*a*, NS1*b*, NS1*c* caused respectively by engines 102*a*, 102*b*, and the zip sound produced at the nose of the aircraft exist as external noise sources, and NS2*a*-NS2*e* caused by air-conditioners and others exist as internal noise sources. These noise sources affect, e.g. seat 105 placed in cabin A, as noises. To be more specific, seat 105 receives noises from noise source NS1*a*-NS1*c* produced by engine 102*a* installed to the wing outside the window (refer to FIG. 1) and airstream sound, and other noises coming from noise sources NS2*a*-NS2*e* caused by air-conditioners. For instance, it can be assumed that the noise from noise source NS1*a* caused by the engine installed to the left wing (shown in FIG. 1) is the greatest noise at seat 105 among the noises coming from noise sources NS1*a*-NS1*c* and NS2*a*-NS2*e*. To achieve the noise reduction efficiently for passengers in each seat, it is required to deal with chiefly the noise that gives the sound environment of the seat the most adverse influence among other noises.

Figure 3:
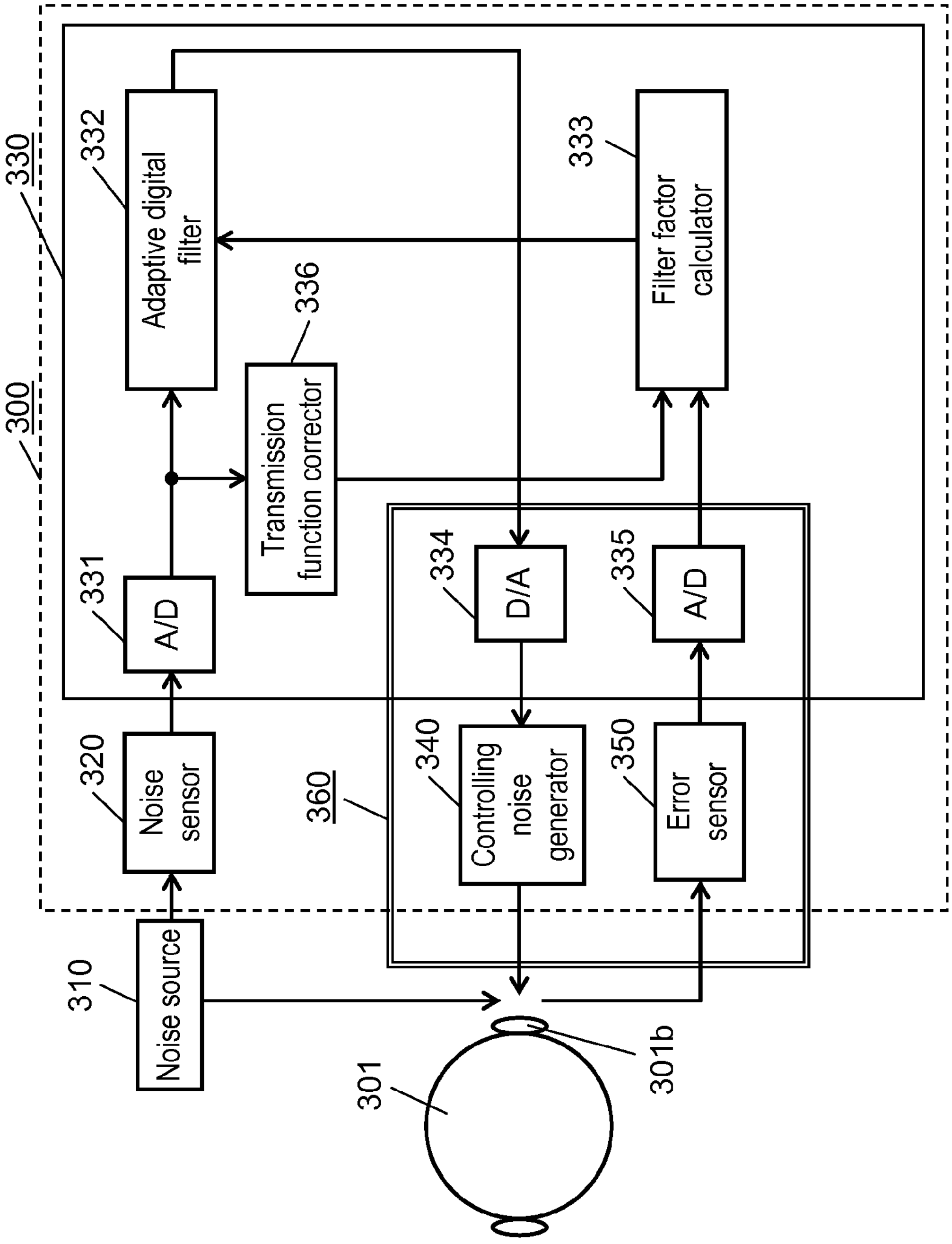
FIG. 3 is a block diagram illustrating a basic structure where an adaptive action of a noise reduction device is carried out in accordance with the first embodiment of the present invention.

The seat in the first class in particular, i.e. in cabin A shown in FIG. 1, forms a shell-like structure, in which audio-video devices such as a television receiver and a radio receiver for a passenger to enjoy a cinema and music, a desk for a businessman, and a power supply to be connected to a personal computer are available. This environment is strongly required to afford the passenger relaxation or concentration of his or her attention on business. The noise reduction in this shell structure is thus greatly required among others. FIG. 3 is a block diagram illustrating a basic structure where an adaptive action (detailed later) of the noise reduction device is carried out in accordance with the first embodiment of the present invention. Noise reduction device 300 is formed of noise sensor 320, noise controller 330, controlling sound generator 340, and error sensor 350. Region 360 surrounded with double-line indicates the region of which transmission function is to be found.

Each structural element discussed above is detailed hereinafter. Noise sensor 320 is a microphone (hereinafter referred to as a noise microphone) for sensing a noise generated by noise source 310, and also senses noise information and converts the information into an electric signal and then outputs the signal.

Noise controller 330 includes A-D converters 331, 335, adaptive digital filter 332, filter-coefficient calculator 333, and D-A converter 334. Noise controller 330 generates a controlling sound signal based on noise information supplied from noise microphone 320 and error information supplied from error sensor 350 so that a sensing error can be minimized.

Controlling sound generator 340 is a control speaker working as a controlling sound output section, and converts the controlling sound signal supplied from D-A converter 334 into a sound-wave and then outputs the sound-wave. Sound generator 340 also generates a controlling sound to be superposed on noises around ear 301*b* of user 301 for reducing the noises.

Error sensor 350 is a microphone (hereinafter referred to as an error microphone) that senses an error sound (residual sound) between the noise generated by noise source 310 and the controlling sound generated by speaker 340, and then converts the error sound into an electric signal before outputting this signal.

Adaptive digital filter 332 is a FIR filter formed of multi-stage taps. Filter coefficients of each tap can be set at any values, and the filer coefficients of adaptive digital filter 332 are adjusted so that the sensing error can be minimized. This sensing error signal supplied from error microphone 350 is input to filter-coefficient calculator 333 via A-D converter 335 in addition to the information supplied from noise microphone 320. To be more specific, a controlling sound signal having a phase opposite to that of the noise generated by noise source 310 is produced at a setting position of error microphone 350, and this controlling sound signal is supplied to controlling sound generator 340 via D-A converter 334.

Transmission function corrector 336 is a FIR filter formed of a multi-stage taps which express a transmission function of range 360. In other words, an output from adaptive digital filter 332 undergoes D-A converter 334 and control speaker 340, thereby generating the controlling sound which then travels through error microphone 350 and A-D converter 335 and finally arrives at filter coefficient calculator 333. The FIR filter expresses the transmission function of this traveling path.

A-D converter 331 A-D converts the noise signal supplied from noise microphone 320, and the resultant signal undergoes adaptive digital filter 332 and transmission function corrector 336, and finally arrives at filter coefficient calculator 333. The travel of the noise signal through corrector 336 allows an output from filter 332 to take the transmission characteristics into account. The transmission characteristics include delay, reflection on an error sound signal which has undergone the A-D conversion and is to be supplied to filter coefficient calculator 333. As a result, an accurate filter coefficient can be calculated.

Error microphone 350 working as the error sensor senses the sound having undergone the noise reduction as an error, and gives feedback to noise reduction device 300 with this error. This feedback allows minimizing noises always at user's ear even if the noise environment is changed.

As shown in FIG. 3, in noise reduction device 300, noise microphone 320 senses a noise generated by noise source 310, and then noise controller 330 processes this noise signal for control speaker 340 to output a controlling sound. This controlling sound has a reversal phase to that of the noise, and is superposed on the noise before the noise arrives at ear 301*b* of user 301. As a result, the noise is reduced. This mechanism is referred to as an adaptive action.

Figure 4:
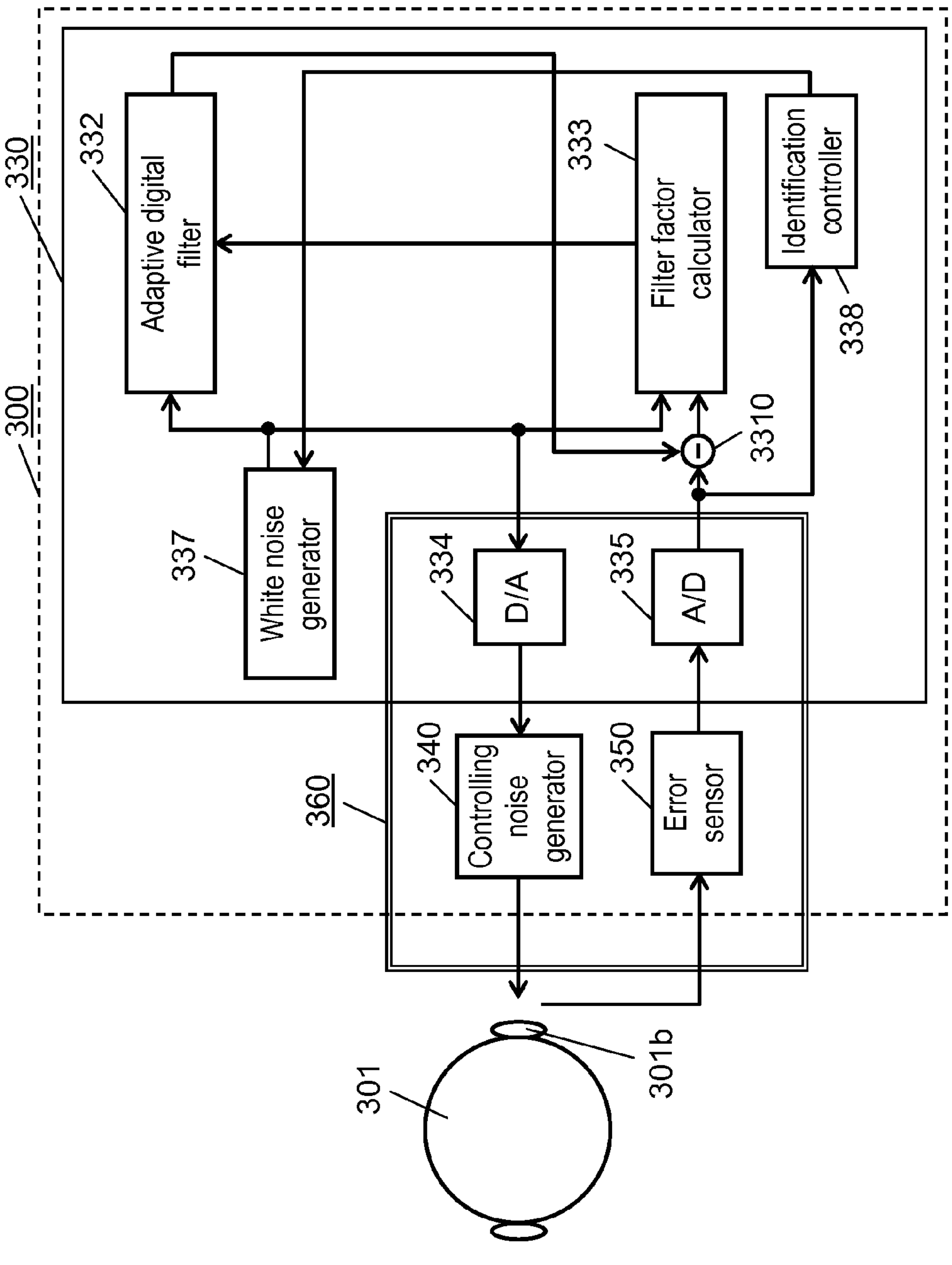
FIG. 4 is a block diagram illustrating a basic structure where an identifying action of the noise reduction device is carried out in accordance with the first embodiment of the present invention.

Next, a way of finding a transmission function of region 360 is described hereinafter. The work for finding the transmission function is referred to as an identifying action relative to the adaptive action shown in FIG. 3. FIG. 4 is a block diagram illustrating a basic structure where the identifying action of the noise reduction device is carried out in accordance with the first embodiment. In the following description, a white noise is used as an identification sound for an identifying action.

During the identifying action, white-noise generator 337 working as an identification sound generator and identification controller 338 working as controlling generator 337 are used. These generator 337 and controller 338 are available in noise controller 330. Adaptive digital filter 332, filter coefficient calculator 333, D-A converter 334, A-D converter 335, controlling sound generator (control speaker) 340, and error sensor (error microphone) 350 are formed of the same components as shown in FIG. 3. Since the identifying action finds the transmission function of range 360, the components particularly used in range 360 are desirably identical to what are shown in FIG. 3.

During the identifying action, noise controller 330 outputs a noise supplied from white noise generator 337 via D-A converter 334. Differentiator 3310 finds a difference between a signal received from error microphone 350 and having undergone the A-D conversion and an output supplied from adaptive digital filter 332. This difference is referred to as an identification difference signal, which then enters filter coefficient calculator 333 together with the output supplied from white noise generator 337. Calculator 333 calculates a filter coefficient such that the identification difference signal can be minimized, and then changes the coefficient of adaptive digital filter 332 accordingly. This mechanism allows calculating coefficients of the FIR filter which expresses the transmission function of region 360.

FIG. 3 shows a structure where the noise generated by noise source 310 enters error microphone 350. During the identifying action, the level of the noise entering error microphone 350 is desirably lower than a level of the white noise supplied from control speaker 340 and entering error microphone 350.

In the environment where multiple noise reduction devices are installed, if white noises generated by the other noise reduction devices during the identifying action enter error microphone 350, the accuracy of the FIR filter of transmission function corrector 336 would be degraded. Identification controller 338 thus should determine, based on A-D converted data of the inputs to microphone 350, whether or not the white noises generated by other noise reduction devices during the identifying action around the subject noise reduction device enter the error microphone. When it is determined that no such white noises enter the error microphone, controller 338 prompts white noise generator 337 to generate a white noise, and then starts the identifying action. This mechanism allows preventing the FIR filter of corrector 336 from degrading in accuracy.

Figure 5:
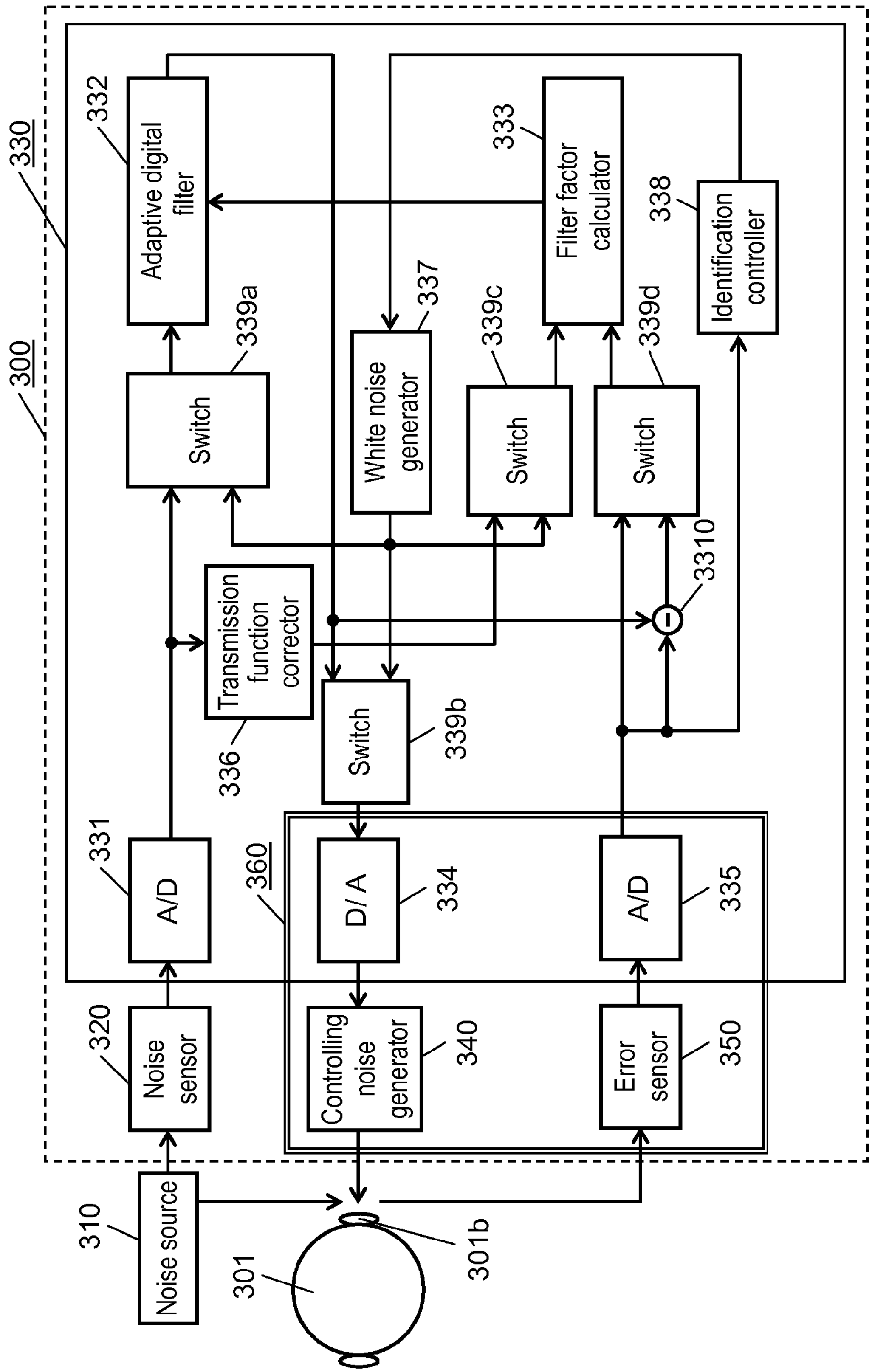
FIG. 5 is a block diagram illustrating a structure where an adaptive action and an identifying action can be switched from each other in the noise reduction device in accordance with the first embodiment of the present invention.
Figure 6:
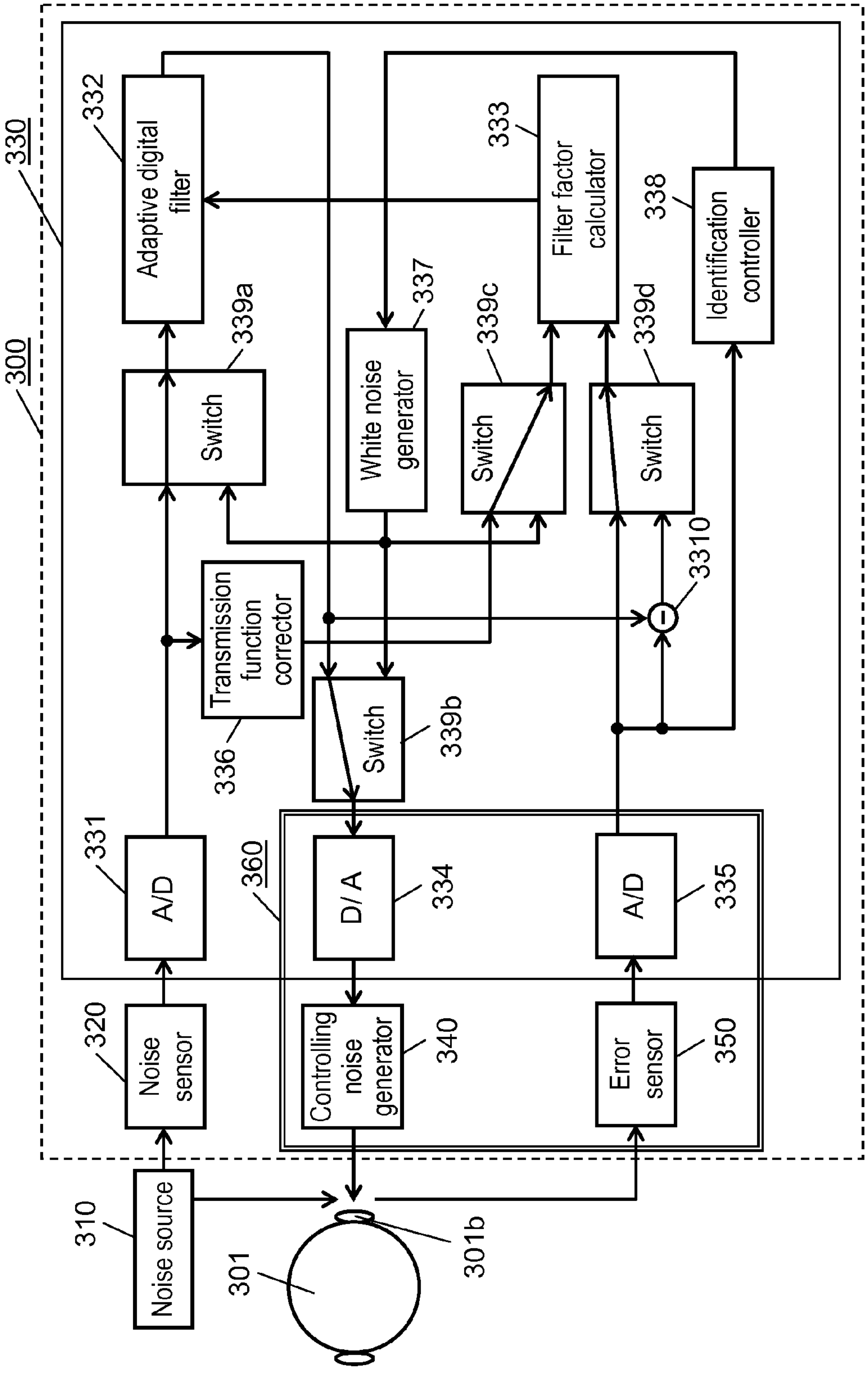
FIG. 6 is a block diagram illustrates a switching operation at the adaptive action of the noise reduction device in accordance with the first embodiment of the present invention.
Figure 7:
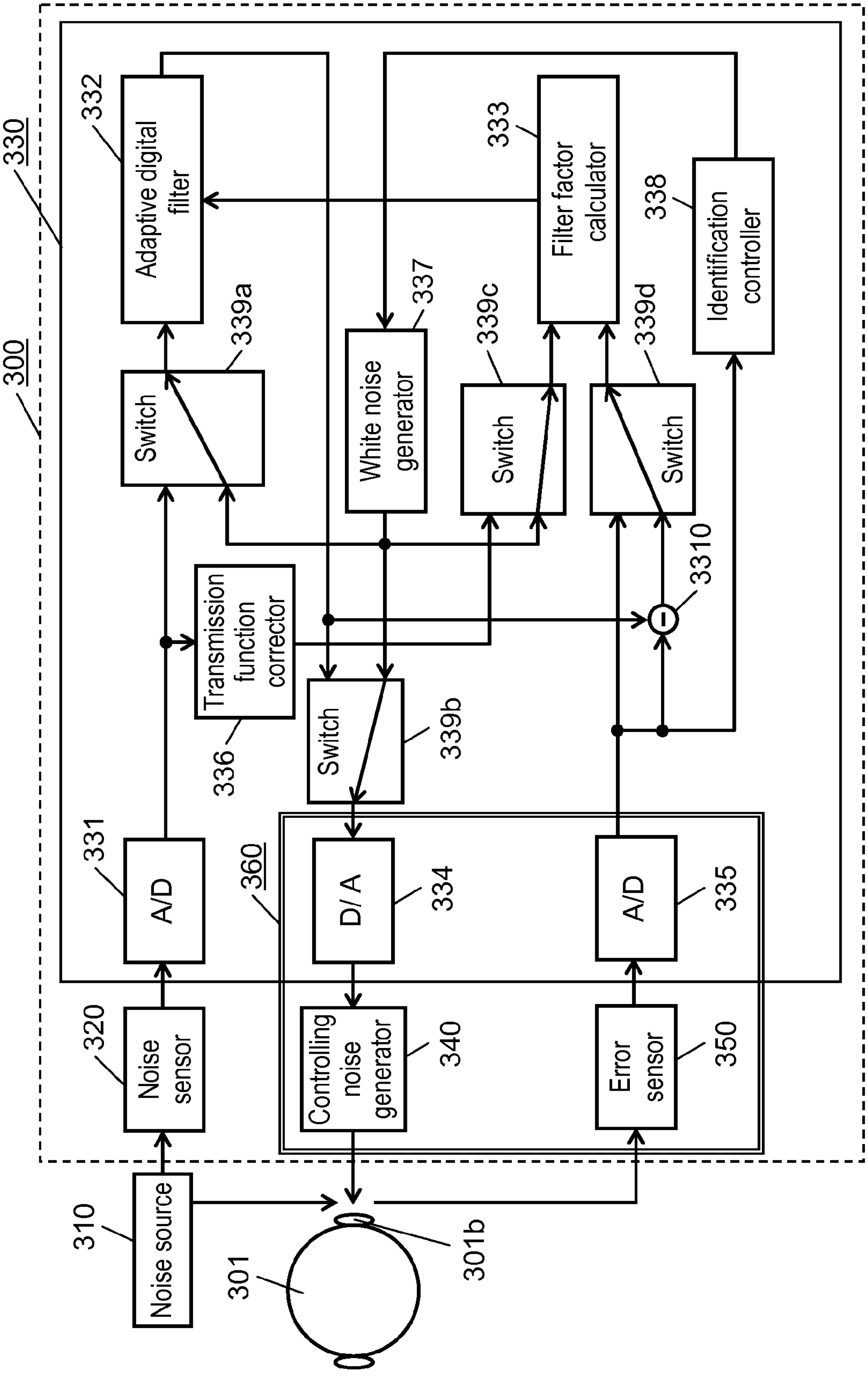
FIG. 7 is a block diagram illustrates a switching operation at the identifying action of the noise reduction device in accordance with the first embodiment of the present invention.

The adaptive action shown in FIG. 3 and the identifying action shown in FIG. 4 can be done within one component by switching switches 339*a*-339*d* supposed to be inserted as shown in FIG. 5. Switch-over of switches 339*a*-339*d* as shown in FIG. 6 makes the structure the same as that shown in FIG. 3, and allows carrying out the adaptive action. Switch-over of switches 339*a*-339*d* as shown in FIG. 7 makes the structure the same as that shown in FIG. 4, and allows carrying out the identifying action.

Next, the case where the noise reduction device in accordance with the first embodiment is installed in a cabin of an aircraft is demonstrated hereinafter with reference to FIG. 8, which is a plan view illustrating major components that form the noise reduction device installed in the cabin of the aircraft.

Figure 8:
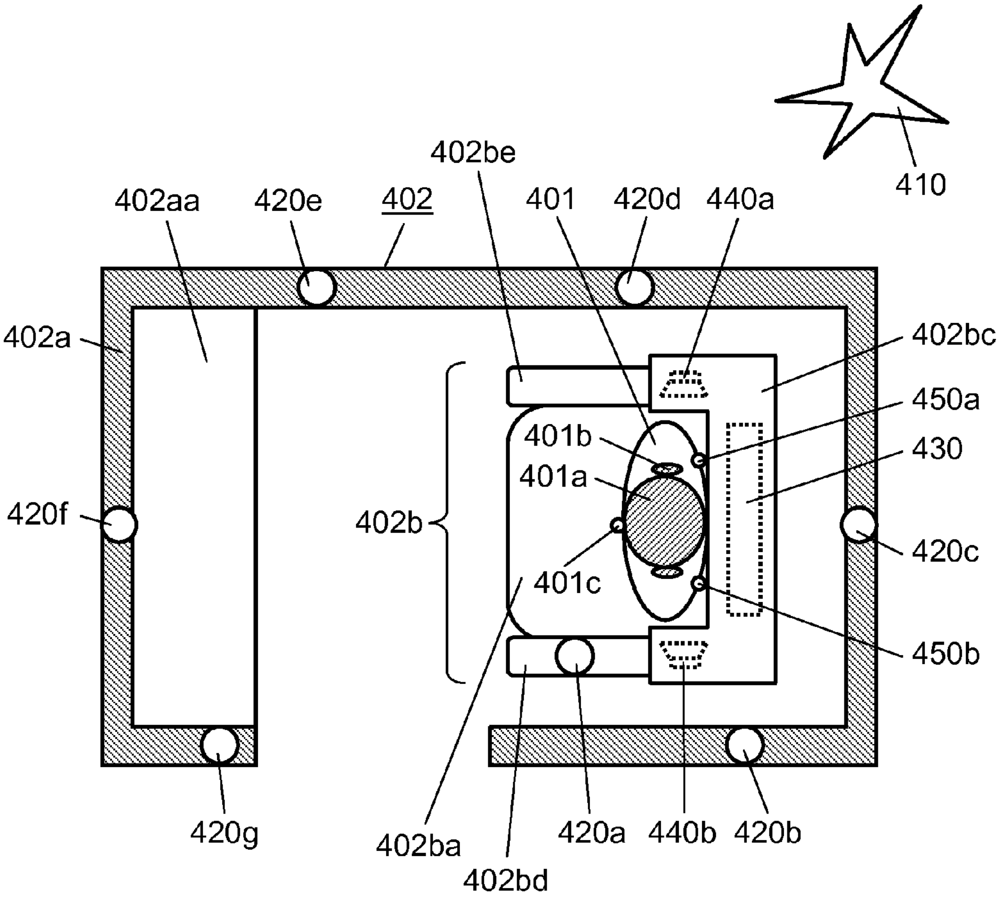
FIG. 8 is a plan view illustrating major components forming the noise reduction device, installed in a cabin of an aircraft, in accordance with the first embodiment of the present invention.

As shown in FIG. 8, the noise reduction device is installed at seat 402 placed in cabin A (refer to FIG. 1). Seat 402 forms a control space in which noise is supposed to be controlled. Seat 402 includes shell section 402*a* which surrounds and occupies a private space for a user by using walls and seat part 402*b* placed within shell section 402*a*. Shell section 402*a* is equipped with shelf 402*aa* confronting a forward section of seat part 402*b*, and shelf 402*aa* can serve as a desk. Seat part 402*b* is formed of a backrest (not shown), headrest 402*bc* and armrests 402*bd*, 402*be*.

Cabin A in the aircraft is affected by noise sources such as the engines mounted to the body, air-conditioners installed in the cabins, and others. Those noise sources generate the noises, which arrive at the outer wall of shell section 402*a* of seat 402. The location of head 401*a* of user 401 seated in seat 402 is defined as a center of the control space within shell section 402*a*. Assuming this center as the control center, the noise reduction device controls over this control space.

In FIG. 8, shell section 402*a* works physically as an acoustic insulator for seat 402 against the noise generated from, e.g. external noise source 410; however, the noise travels into shell section 402*a* and arrives at head 401*a* (control center) of user 401 seated in seat 402*a*. In a case of the aircraft where various noise sources are available and it is hard to distinguish which source is a major one, multiple non directional microphones are placed in or around shell section 402*a* (control space). FIG. 8 shows an example of placing noise microphones 420*a*-420*g* (corresponding to noise microphone 320 shown in FIG. 3) at given spots, control speakers 440*a*, 440*b* (corresponding to control speaker 340 shown in FIG. 3) at seat 402, and error microphones 450*a*, 450*b* (corresponding to error microphone 350 shown in FIG. 3) at seat 402.

In this case the presence of two control speakers and two error microphones needs identifying actions shown in FIG. 4 for each speaker and microphone. For instance, control speaker 440*a* outputs a white noise which arrives at error microphones 450*a*, 450*b*, where the white noise is caught as a signal respectively. Base on the signals, identification error signals are formed for calculating a filter coefficient. Then control speaker 440*b* outputs a white noise, and a filter coefficient (transmission function) is calculated in a similar way. In the foregoing case, therefore, four transmission functions are obtained.

Figure 9:
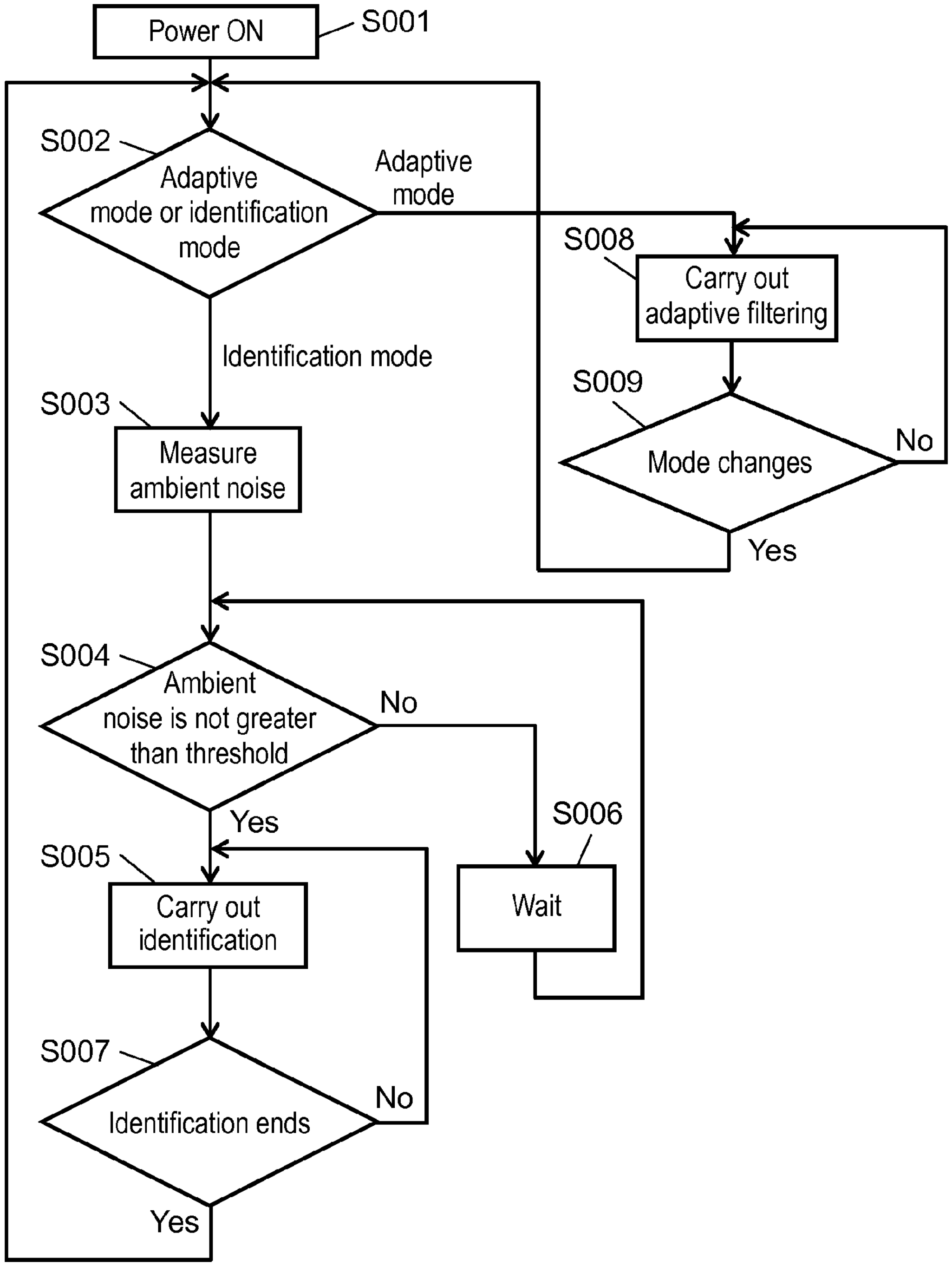
FIG. 9 is a flowchart showing an operation of the noise reduction device in accordance with the first embodiment of the present invention.

FIG. 9 is a flowchart showing an operation of the noise reduction device in accordance with the first embodiment of the present invention. Each step of the flowchart is demonstrated hereinafter. Turn on the power supply of the noise reduction device, and then the step moves from S001 to S002, where an adaptive mode or an identification mode is selected. The selection can be done this way: the identification mode is selected at an initial starting, or a user can select one of them with a switch. The adaptive mode refers to an adaptive action, and the identification mode refers to an identifying action.

In the case of selecting the identification mode, an ambient noise is measured in step S003, and the step moves on to S004 where the measured noise is determined whether or not it exceeds a given threshold. For instance, in FIG. 4, identification controller 338 determines whether or not the ambient noise exceeds the threshold based on the ambient noise supplied from error microphone 350 and having undergone A-D conversion.

When the ambient noise is not greater than the threshold, a white noise is generated and then the identifying action is carried out in step S005. Steps S005, S006 and S007 are repeated until the identifying action ends.

When step S004 determines that the ambient noise exceeds the threshold, the step moves on to step S006 where a given waiting time passes before the step returns to step S004, where controller 338 determines again whether or not the ambient noise is not greater than the threshold. The waiting time in step S006 is set at the time when the noise reduction device generates the white noise. This setting allows preventing another noise reduction device from starting another identifying action although the subject device still engages in the identifying action, because this another action will adversely affect the subject noise reduction device.

In the case of selecting the adaptive mode in step S002, step S008 carries out an adaptive filtering, and step S009 monitors the change in the action mode. The adaptive filtering is repeated as long as no changes happen in the action mode. When the action mode changes to the identification mode, the step returns to step S002 and then moves on to step S003. The adaptive filtering in this context refers to this: an optimum filter coefficient is calculated by filter coefficient calculator 333, and this optimum coefficient is set at adaptive digital filter 332 for carrying out the adaptive filtering.

In the environment where multiple noise reduction devices are installed, the foregoing operation allows preventing the white noises generated by other noise reduction devices during the identifying actions from traveling into error microphone 350. Otherwise the accuracy of the FIR filter in transmission function corrector 336 is degraded. When the white noises generated during the identifying actions of other noise reduction devices are not greater than the threshold, these other noise reduction devices can undergo the identifying action at the same time as the subject device, so that the time for identifying action can be shortened.

Exemplary Embodiment 2

Figure 10:
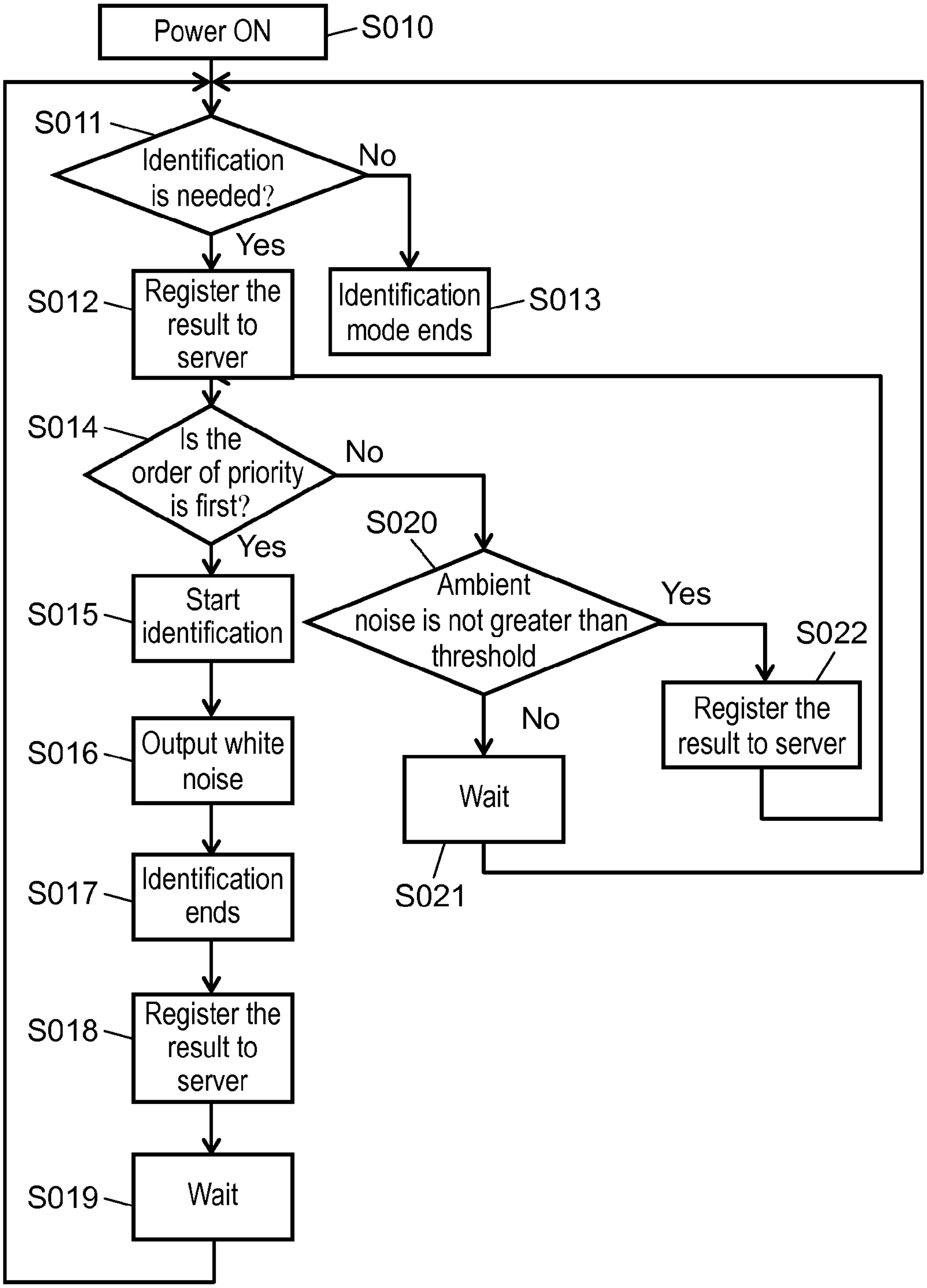
FIG. 10 is a flowchart showing an operation of a noise reduction device in accordance with a second embodiment of the present invention.
Figure 11:
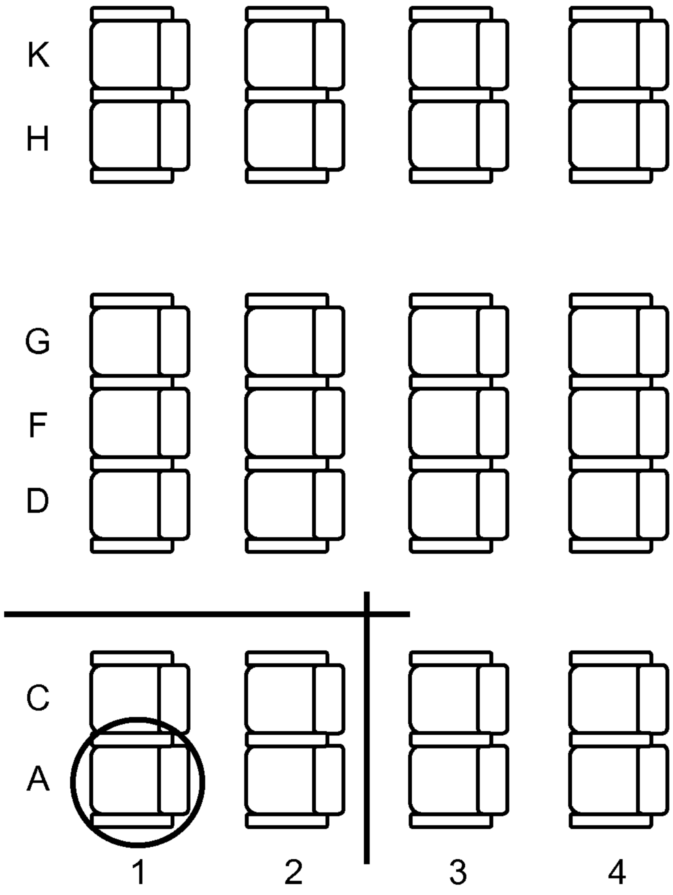
FIG. 11 illustrates a seat-arrangement, where the noise reduction devices in accordance with the second embodiment are installed, and the seat of which noise reduction device engages in the identifying action at a given timing.
Figure 12:
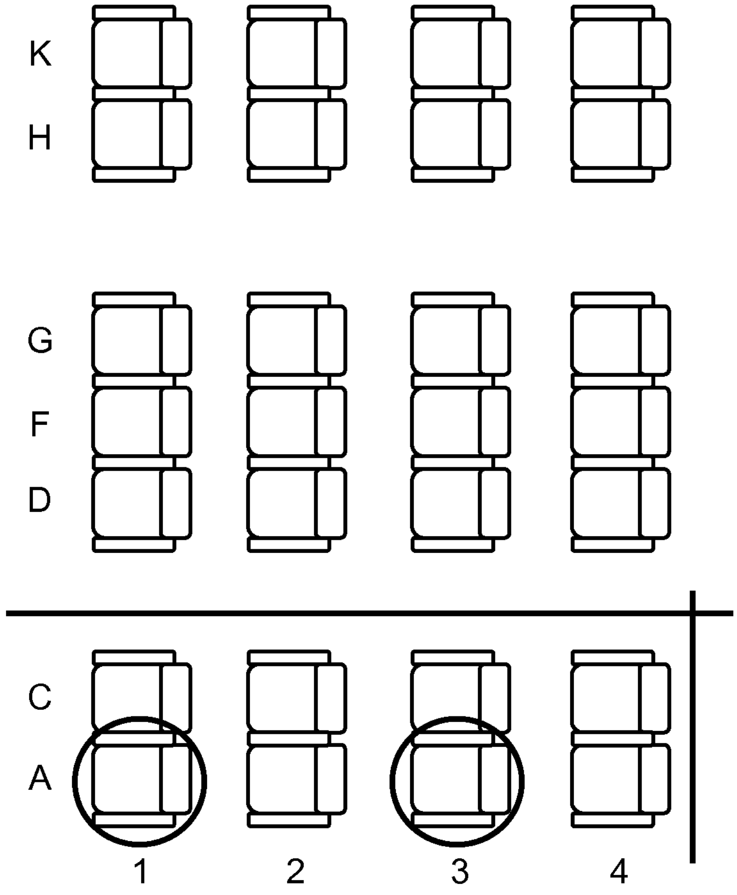
FIG. 12 illustrates a seat-arrangement, where the noise reduction devices in accordance with the second embodiment are installed, and the seats of which noise reduction devices engage in the identifying action at given timings.
Figure 13:
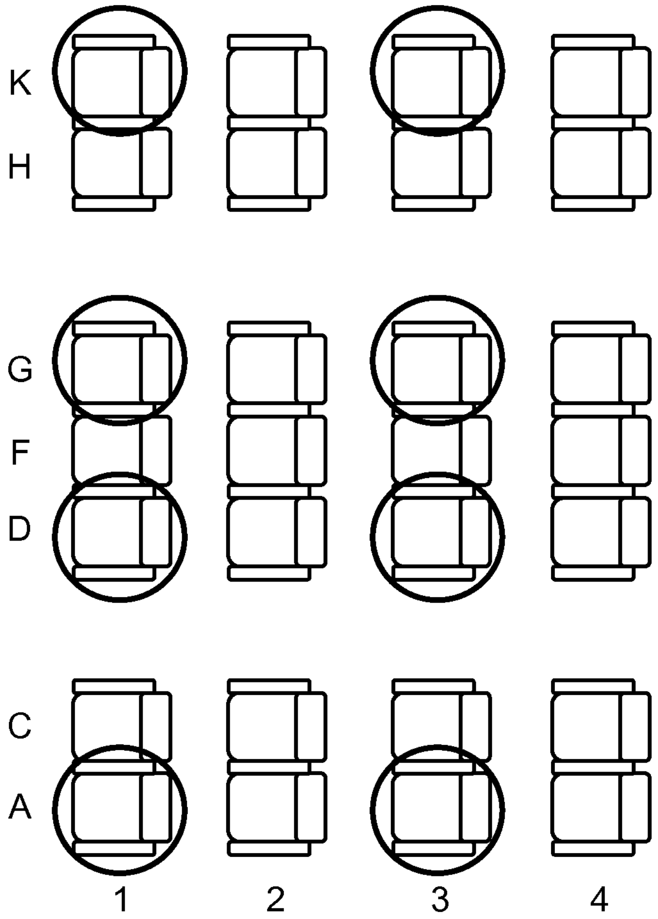
FIG. 13 illustrates a seat-arrangement, where the noise reduction devices in accordance with the second embodiment are installed, and the seats of which noise reduction devices engage in the identifying action at given timings.

FIG. 10 is a flowchart showing an operation of a noise reduction device in accordance with the second embodiment of the present invention. In this second embodiment, multiple noise reduction devices are installed at each one of the seats in the aircraft for forming a noise reduction system. The flowchart shown in FIG. 10 describes actions in the respective seats, and the information, e.g. seat numbers and the order of priority for identification, of these multiple seats shown in FIG. 11 is controlled by a server (not shown), i.e. a system controller 14 (in FIG. 2). In FIG. 11, the seats are arranged such that the first, second, third, and fourth rows are arranged from the front to the rear, and line A, line C . . . , and line K from the left to the right. For instance, the front left seat is called seat 1A, and the seat on the second row and line H is called seat 2H. Each step shown in FIG. 10 is demonstrated hereinafter.

Turn on the power supply of the noise reduction device for move the step from S010 to S011, where it is determined whether or not identification is needed. This determination can be done this way: at the initial starting the identification should be done, or it is done, e.g. once in a month, based on a periodical instruction supplied from the server.

In the case of requiring the identification, the step moves on to S012 where seat numbers that require the identification are registered. Among these registered seat numbers step S014 retrieves an order of priority, and then step S015 starts identifying ("Yes", i.e. positive branch from decision block S014) a firstly prioritized seat. A way of prioritizing the seats is this: for instance in the case of seat arrangement shown in FIG. 11, seat 1A is prioritized firstly, seat 2A is prioritized secondly, and seat 3A is thirdly prioritized, and so on, then the seats on line C are prioritized accordingly. Seat 4K is thus prioritized last.

After starting the identifying action in step S015, then a white noise is output in step S016, and the identifying action ends in step S017. Step S018 registers the information of ending the identification to the server. A waiting time lapses in step S019 for adjusting time until, e.g. all the noise reduction devices, which have been registered to the server as they need identification, have undergone the identifying action respectively.

In step S014, when the subject seat is not prioritized firstly ("No", i.e. negative branch from decision block S014), the ambient noise is measured in step S020 and when the noise level is not greater than the threshold, i.e. "Yes" indicated by the positive branch from decision block S020, step S022 registers the subject seat number to the server, and the step returns to S014. In step S014 when the subject seat number is first prioritized among other seat numbers of which ambient noises are not greater than the threshold, the step moves on to step S015 for starting the identification, and then takes the same steps as discussed previously. In step S020 the ambient noise level of the subject seat exceeds the threshold, i.e. "No" indicated by a negative branch from decision block S020, the step moves on to S021, where the waiting time lapses for adjusting identification times as done in step S019. The step then returns to S011.

FIG. 11 shows schematically a sequence of identifications. The instance shown in FIG. 11 describes that every seat needs identification, and the seats (1C, 2A, and 2C) adjacent to subject seat 1A, which generates a white noise, receive ambient noises greater than the threshold, and the other seats receive ambient noises not greater than the threshold.

Figure 14:
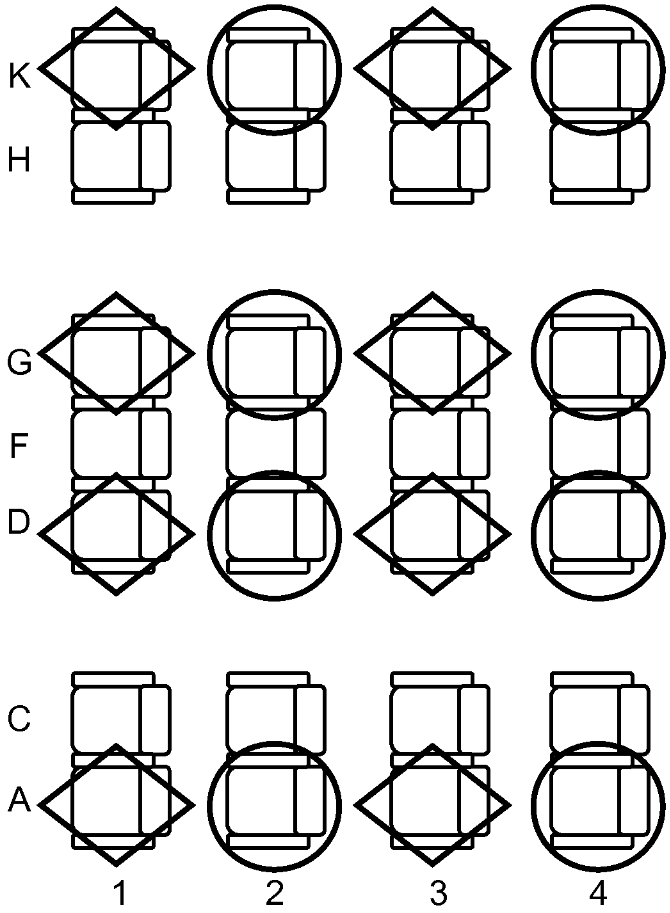
FIG. 14 illustrates a seat-arrangement, where the noise reduction devices in accordance with the second embodiment are installed, and the seats of which noise reduction device engage in the identifying action at given timings.
Figure 15:
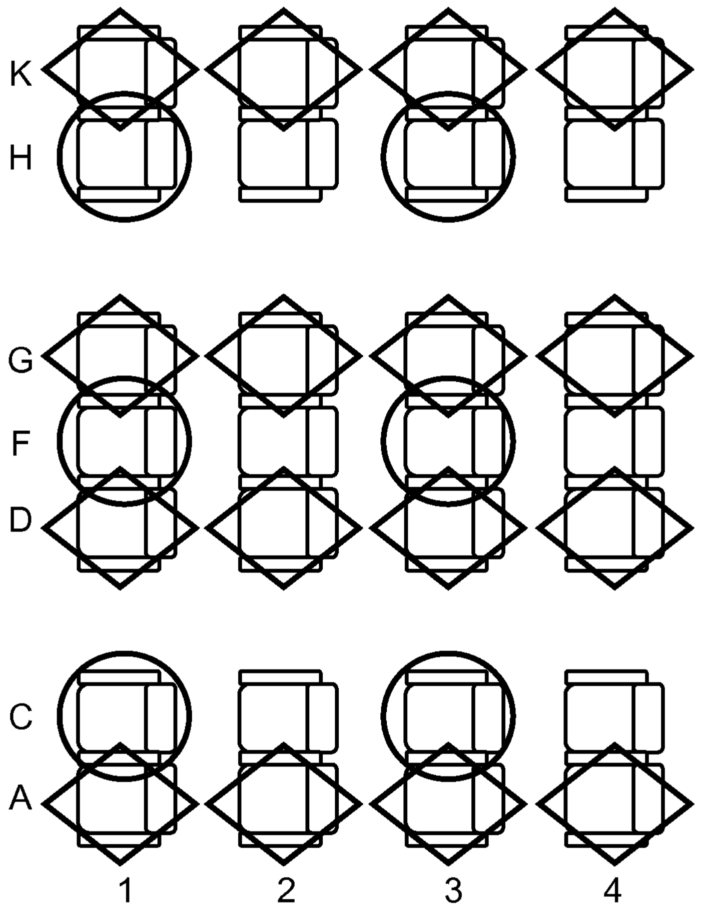
FIG. 15 illustrates a seat-arrangement, where the noise reduction devices in accordance with the second embodiment are installed, and the seats of which noise reduction devices engage in the identifying action at given timings.
Figure 16:
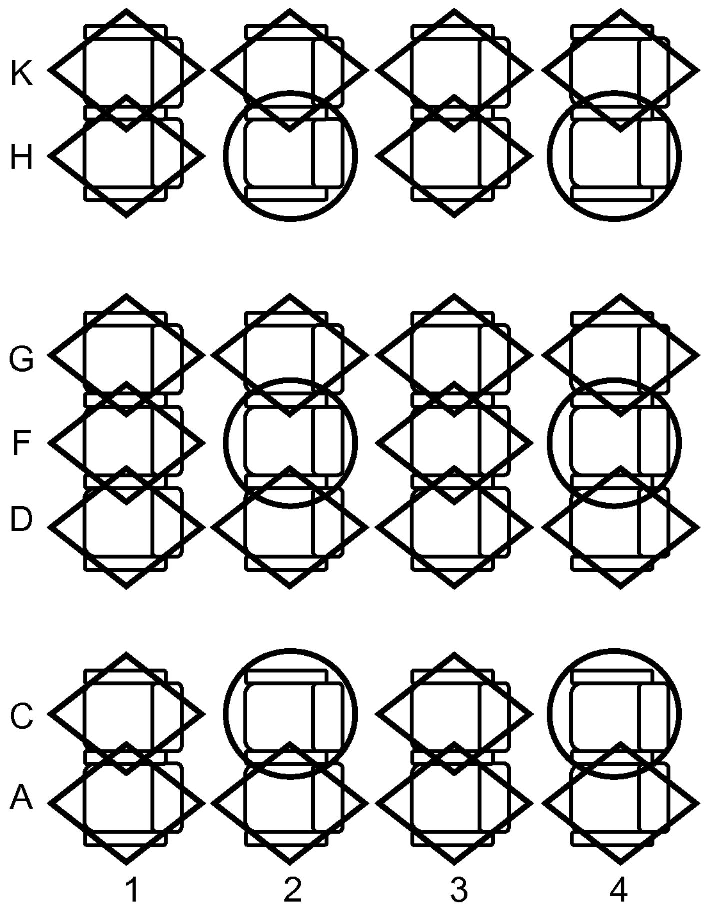
FIG. 16 illustrates a seat-arrangement, where the noise reduction devices in accordance with the second embodiment are installed, and the seats of which noise reduction devices engage in the identifying action at given timings.
Figure 17:
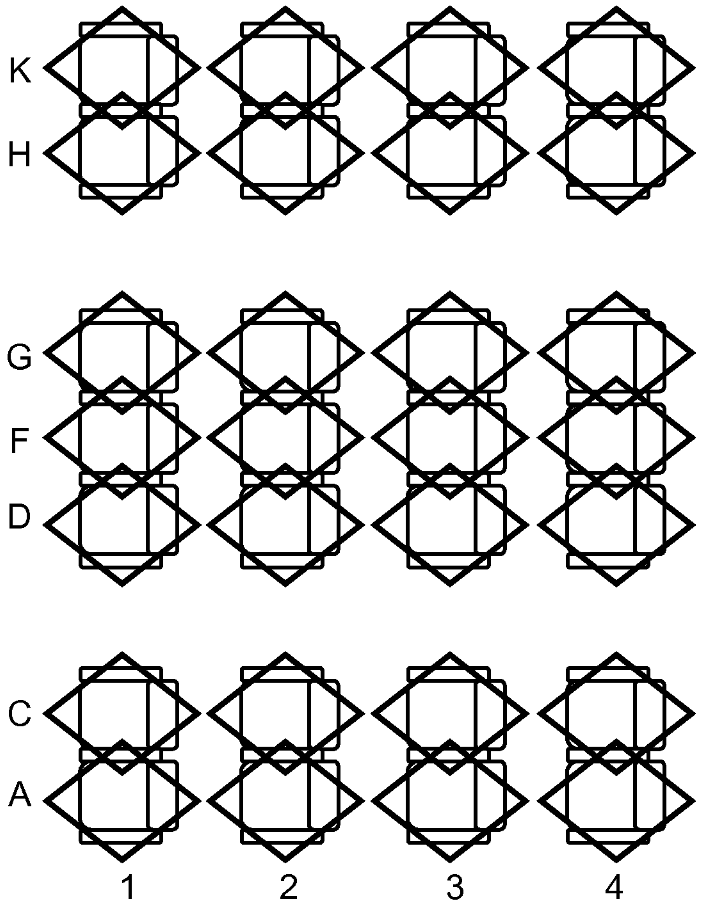
FIG. 17 illustrates a seat-arrangement, where the noise reduction devices in accordance with the second embodiment are installed, and the seats of which noise reduction devices engage in the identifying action at given timings.
Figure 18:
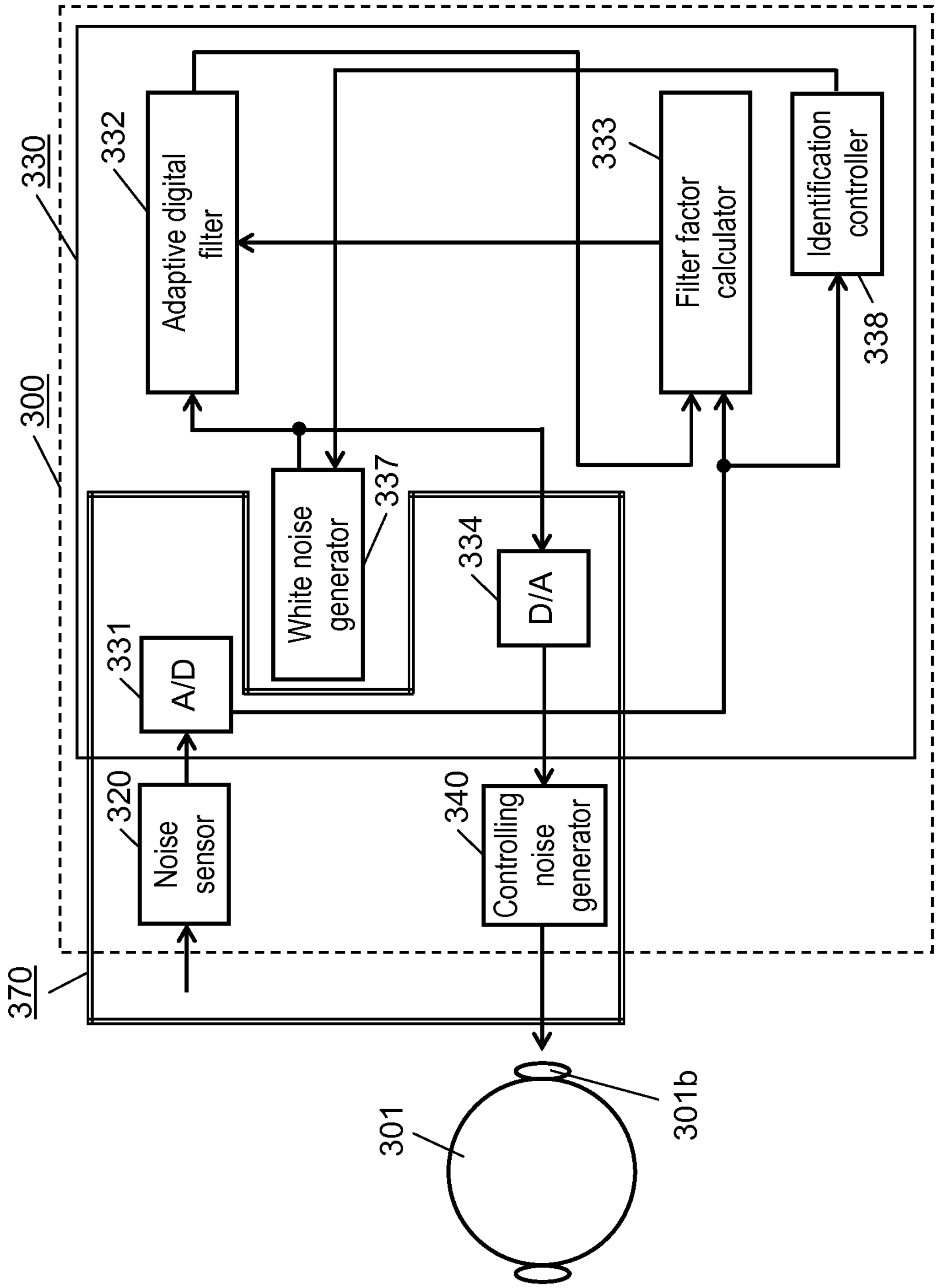
FIG. 18 is a block diagram illustrating a structure in which a noise microphone of the noise reduction device in accordance with the second embodiment is identified.

First, seat 1A having a higher priority than others starts identifying, and outputs the white noise (circled seat shown in FIG. 11). Then seat 3A having the next priority starts identifying. In a case where a time difference from the start of identifying seat 1A to the start of identifying seat 3A is substantially shorter than an identification time, the circled seats shown in FIG. 12 undergo the identifying action simultaneously. This can be applied to other seats, namely, when the time difference from the start of identifying a seat to the start of identifying another seat is substantially shorter than an identification time, the circled seats shown in FIG. 13 undergo the identifying actions almost simultaneously. In FIG. 14-FIG. 17, the seats having already undergone the identifying action are marked with diamond-shaped signs. The circled seats shown in FIG. 14 are to undergo the identifying action next, and then the circled seats in FIG. 15, FIG. 16 are to undergo the identifying action sequentially. Finally as shown in FIG. 17, all the seats have undergone the identifying action.

For instance, an identifying action takes five minutes, and a time difference between the seats which undergo the identifying actions at about the same time is ten seconds, then the waiting time in steps S019 and S021 can be set at minimum 5 minutes and 10 seconds after the start of identifying action of the seat firstly prioritized.

According to this second embodiment, the determination of whether or not the ambient noise exceeds the threshold is done only at the start of the identifying action, so that influence of the white noise generated from the other seats is left out of consideration after the start of the identifying action. However, since a relation between the control speaker and the error microphone is usually kept constant at each seat, the identifying action of seat 1A is affected little by the white noise generated from seat 3A, and the identifying action of seat 3A is affected little by the white noise generated from seat 1A.

However, in a case where a white noise level entering the error microphone of the subject seat during the identifying action is desirably not lower than that of a white noise level from another seat by at least 20 dB, the threshold can be set at 23 dB for having a greater tolerance.

In a case where the relation between the control speaker and the error microphone differs greatly in respective seats, the white noise generated from another seat will affect the identifying action of the subject seat. In such a case, when another seat starts identifying action, the ambient noise of the subject seat is measured again even when the subject seat engages in the identifying action. If this re-measurement finds that the ambient noise exceeds the threshold, this another seat can cancel its identifying action. In the case of the cancellation, the same waiting time as those in step S019 or S021 can be set for waiting a determination (step S011) whether or not another identifying action is necessary.

In the environment where multiple noise reduction devices are installed, the structure discussed above allows preventing the FIR filter of the transmission function corrector from degrading in accuracy. This degradation in accuracy of the FIR filter is caused by the white noise, which is generated during the identifying action of noise reduction devices other than the subject noise reduction device, entering the error microphone. The other noise reduction devices, of which white noise levels are not greater than the threshold, can undergo the identifying actions simultaneously, so that the identification time can be shortened.

In this embodiment, a white noise is used as an identification sound to be used for the identifying action; however, it is not restricted to the white noise, e.g. a pink noise can be work as well. Identification sounds restricted within a certain frequency bandwidth can be generated temporally shifted. In this case, only the sound in the same frequency bandwidth as that of the identification sound generated at the subject seat can be determined to be an ambient noise.

An instance, where the identifying action is done for targeting the transmission function of range 360, is described previously as shown in FIG. 4. The mechanism of this instance can be applied to the case where the identifying action is done to the transmission function of range 370 shown in FIG. 18, i.e. the identifying action is done to the noise microphone instead of the error microphone. Assume that the transmission functions of the control speaker and the noise microphone have been obtained in advance, and then the noise microphone can collect in-aircraft noises such as NS1*a*-NS1*c*, NS2*a*-NS2*c* in addition to the controlling sound generated by the control speaker during the adaptive action. In this case, the in-aircraft noises can be accurately separated before they are supplied to A-D converter 331, so that the controlling sound can be prevented from entering the noise microphone. As a result, an adverse affect to the noise reduction can be removed. The transmission functions of ranges 360 and 370 can undergo the identifying actions simultaneously.

In the exemplary embodiments discussed above, when the transmission function between the control speaker and the error microphone is identified, the ambient noise level is sensed by the error microphone and compared with the threshold; however, the ambient noise level can be sensed by the noise microphone. To the contrary when the transmission function between the control speaker and the noise microphone is identified, the ambient noise level can be sensed by the error microphone and compared with the threshold. A microphone specialized in sensing the ambient noise level can be installed.

In the embodiments discussed above, the comparison between the ambient noise level and the threshold is done at the start of the identifying action; however, the comparison can be done during the identifying action.

What is claimed is:

1. A noise reduction device comprising:

a noise sensor for sensing a noise;

a controlling sound output section for generating a controlling sound based on a controlling sound signal, which controlling sound is to be superposed on the noise at a control center of a control space for reducing the noise;

a noise controller for generating the controlling sound signal; and an error sound sensor for sensing an error sound between the noise and the controlling sound at the control center, wherein the noise controller includes an identification sound generator and an identification controller, wherein when an acoustic transmission function covering a path from the controlling sound output section to one of the error sound sensor and the noise sensor is identified by outputting an identification sound from the controlling sound output section and then by sensing the identification sound with the one of the error sound sensor and the noise sensor, the identification controller prompts the identification sound generator to generate the identification sound for identifying the acoustic transmission function provided that an ambient noise level sensed by the one of the error sound sensor and the noise sensor is not greater than a given threshold.

2. The noise reduction device of claim 1, wherein when an ambient noise level sensed by the error sound sensor or the noise sensor is greater than the given threshold, the identification controller waits for a given time, and then determines whether or not the ambient noise level is not greater than the given threshold.

3. The noise reduction device of claim 2, wherein the given time is a time necessary for the identification.

4. The noise reduction device of claim 1, wherein in an environment where a plurality of noise reduction devices are installed, and when a white noise attributed to identification operation of another noise reduction device sensed by one of the error sound sensor and the noise sensor is not greater than the given threshold, the identification controller identifies the acoustic transmission function by generating the identification sound from the identification sound generator.

5. A noise reduction system comprising:

a plurality of noise reduction devices as defined in claim 1; and a server for controlling whether or not the plurality of noise reduction devices carry out identification of the acoustic transmission function, wherein when the plurality of noise reduction devices included in the noise reduction system start respective identification operations according to a predetermined order of priority at intervals substantially shorter than a time necessary for the identification, any of the noise reduction devices next in the order starts the identification operation when an ambient noise level sensed by one of the error sound sensor and the noise sensor is not greater than a given threshold, and the start of the identification operation is registered to the server, and the noise reduction device next in the order starts the identification operation after a waiting period of given time when the ambient noise level sensed by the one the error sound sensor and the noise sensor is greater than the given threshold.

6. The noise reduction system of claim 5, wherein the given time is a time necessary for the identification.

7. The noise reduction system of claim 6, wherein each one of the plurality of noise reduction devices is disposed at each one of seats in an aircraft.

8. The noise reduction system of claim 5, wherein each one of the plurality of noise reduction devices is disposed at each one of seats in an aircraft.

9. A noise reduction system comprising:

a plurality of noise reduction devices as defined in claim 2; and a server for controlling whether or not the plurality of noise reduction devices carry out identification of the acoustic transmission function, wherein when the plurality of noise reduction devices included in the noise reduction system start respective identification operations according to a predetermined order of priority at intervals substantially shorter than a time necessary for the identification, any of the noise reduction devices next in the order starts the identification operation when an ambient noise level sensed by one of the error sound sensor and the noise sensor is not greater than a given threshold, and the start of the identification operation is registered to the server, and the noise reduction device next in the order starts the identification operation after a waiting period of given time when the ambient noise level sensed by the one the error sound sensor and the noise sensor is greater than the given threshold.

10. The noise reduction system of claim 9, wherein each one of the plurality of noise reduction devices is disposed at each one of seats in an aircraft.

11. The noise reduction system of claim 9, wherein the given time is a time necessary for the identification.

12. The noise reduction system of claim 11, wherein each one of the plurality of noise reduction devices is disposed at each one of seats in an aircraft.

13. A noise reduction system comprising:

a plurality of noise reduction devices as defined in claim 3; and a server for controlling whether or not the plurality of noise reduction devices carry out identification of the acoustic transmission function, wherein when the plurality of noise reduction devices included in the noise reduction system start respective identification operations according to a predetermined order of priority at intervals substantially shorter than a time necessary for the identification, any of the noise reduction devices next in the order starts the identification operation when an ambient noise level sensed by one of the error sound sensor and the noise sensor is not greater than a given threshold, and the start of the identification operation is registered to the server, and the noise reduction device next in the order starts the identification operation after a waiting period of given time when the ambient noise level sensed by the one the error sound sensor and the noise sensor is greater than the given threshold.

14. The noise reduction system of claim 13, wherein each one of the plurality of noise reduction devices is disposed at each one of seats in an aircraft.

15. The noise reduction system of claim 13, wherein the given time is a time necessary for the identification.

16. The noise reduction system of claim 15, wherein each one of the plurality of noise reduction devices is disposed at each one of seats in an aircraft.

17. A noise reduction system comprising:

a plurality of noise reduction devices as defined in claim 4; and a server for controlling whether or not the plurality of noise reduction devices carry out identification of the acoustic transmission function, wherein when the plurality of noise reduction devices included in the noise reduction system start respective identification operations according to a predetermined order of priority at intervals substantially shorter than a time necessary for the identification, any of the noise reduction devices next in the order starts the identification operation when an ambient noise level sensed by one of the error sound sensor and the noise sensor is not greater than a given threshold, and the start of the identification operation is registered to the server, and the noise reduction device next in the order starts the identification operation after a waiting period of given time when the ambient noise level sensed by the one the error sound sensor and the noise sensor is greater than the given threshold.

18. The noise reduction system of claim 17, wherein each one of the plurality of noise reduction devices is disposed at each one of seats in an aircraft.

19. The noise reduction system of claim 17, wherein the given time is a time necessary for the identification.

20. The noise reduction system of claim 19, wherein each one of the plurality of noise reduction devices is disposed at each one of seats in an aircraft.

* * * * *